US00PP28203P3

(12) United States Plant Patent
Zaiger et al.

(10) Patent No.: US PP28,203 P3
(45) Date of Patent: Jul. 18, 2017

(54) PEACH TREE NAMED 'RICH PRIDE'

(50) Latin Name: *Prunus persica*
Varietal Denomination: Rich Pride

(71) Applicants: Gary Neil Zaiger, Modesto, CA (US); Leith Marie Gardner, Modesto, CA (US); Grant Gene Zaiger, Modesto, CA (US)

(72) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 0 days.

(21) Appl. No.: 13/986,287

(22) Filed: Apr. 19, 2013

(65) Prior Publication Data

US 2014/0317797 P1 Oct. 23, 2014

(51) Int. Cl.
*A01H 5/08* (2006.01)

(52) U.S. Cl.
USPC ..... Plt./197
CPC ..... *A01H 5/0868* (2013.01)

(58) Field of Classification Search
USPC ..... Plt./197
CPC ..... A01H 5/0868
See application file for complete search history.

*Primary Examiner* — Keith Robinson

(57) ABSTRACT

A new and distinct variety of peach tree (*Prunus persica*). The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Vigorous, upright growth of tree.
2. Regular and productive bearer of large size fruit.
3. Fruit with an attractive red skin color.
4. Fruit with firm, yellow flesh.
5. Fruit with very good flavor and eating quality.
6. Fruit with good storage and handling quality.

1 Drawing Sheet

Botanical designation: *Prunus persica.*
Variety denomination: 'Rich Pride'.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of peach tree was originated and asexually. reproduced by us in our experimental orchard located near Modesto, Stanislaus County, Calif.

Prior Varieties

Among the existing varieties of peach trees, which are known to us, and mentioned herein, 'Rich May' Peach (U.S. Plant Pat. No. 7,432), 'Super Rich' Peach (U.S. Plant Pat. No. 9,860), 'Sunnirich' Peach (U.S. Plant Pat. No. 21,567) and our proprietary non-patented peach seedling selections with the field identification numbers '59Z695', '226LK505' and '217LF353'.

STATEMENT REGARDING FEDERALLY SPONSORED RESEARCH AND DEVELOPMENT

Not applicable.

ORIGIN OF THE VARIETY

The new and distinct variety of peach tree (*Prunus persica*) was originated by us in our experimental orchard located near Modesto, Calif. as a first generation cross between our proprietary non-patented peach seedling selections with the field identification numbers '59Z695' and '226LK505'. The seed parent '59Z695' peach (non-patented) originated from a cross of 'Rich May' Peach (U.S. Plant Pat. No. 7,432) and 'Super Rich' Peach (U.S. Plant Pat. No. 9,860). The pollen parent '226LK505' originated from seed of an open pollinated non-patented peach seedling selection '217LF353'. A large number of seed from this first generation cross were grown and maintained on their own root system and under close and careful observation one such seedling, which is the present variety, exhibited desirable fruit and tree characteristics and was selected in 2003 for asexual propagation and commercialization.

ASEXUAL REPRODUCTION OF THE VARIETY

In 2003 asexual reproduction of the new and distinct variety of peach tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

A new and distinct variety of peach tree (*Prunus persica*) is of large size, vigorous, upright growth and a regular and productive bearer of large, yellow flesh, clingstone fruit. The fruit is further characterized by having an attractive red skin color, very good flavor and eating quality and being relatively uniform in size throughout the tree. In comparison to its seed parent '59Z695' peach (non-patented) the fruit of the new variety has a more attractive red skin color and is approximately 32 days later in maturity. In comparison to its pollen parent '226LK505' peach (non-patented) the fruit of the new variety is approximately 3 days earlier in maturity. In comparison to the commercial variety 'Sunnirich' Peach (U.S. Plant Pat. No. 21,567), the fruit of the new variety is larger in size, has a more attractive red skin color and is approximately 7 days earlier in maturity.

DESCRIPTION OF THE PHOTOGRAPH

The accompanying color photographic illustration shows typical specimens of the foliage and fruit of the present new peach variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 9 year old tree and the colors are as nearly true as is reasonably possible in a color representation of this type.

DESCRIPTION OF THE VARIETY

The following is a detailed botanical description of the new variety of peach tree, its flowers, foliage and fruit, as based on observations of 9 year old specimens grown near Modesto, Calif., with color in accordance with Munsell Book of Color published in 1958.

Tree:

*Size*.—Large, usually pruned to 3 to 3.5 meters in height and width for economical harvesting of fruit. Size varies with different cultural practices.

*Vigor*.—Vigorous, growth of 1.5 to 2 meters the first growing season. Varies slightly with soil type, fertility of soil and climatic conditions.

*Form*.—Upright, usually pruned to vase shape.

*Branching habit*.—Upright, crotch angle approximately 30°, increases with heavy crop load.

*Productivity*.—Productive, thinning and spacing of fruit necessary for desired marketable size. Fruit set varies with climatic conditions during bloom time.

*Bearer*.—Regular, has had adequate fruit set 7 consecutive years. No alternate bearing observed.

*Fertility*.—Self-fertile.

*Density*.—Medium dense, pruning to vase shape desirable for sunlight penetration to center of tree to enhance fruit color and health of fruit wood.

*Hardiness*.—Hardy in all stone fruit growing areas of California. Tree grown in USDA Hardiness Zone 9. Winter chilling requirement approximately 850 hours at or below 45° F.

Trunk:

*Size*.—Large. Average circumference 53.3 cm at 30.5 cm above ground on a 9 year old tree.

*Stocky*.—Medium stocky.

*Texture*.—Medium shaggy, becoming rougher with age.

*Color*.—Varies from 2.5Y 4/2 to 5Y 4/2.

Branches:

*Size*.—Medium. Average circumference 14.2 cm at 1.1 meters above ground. Crotch angle approximately 30°, increases with heavy crop load.

*Surface texture*.—New growth relatively smooth. Mature growth medium rough, roughness increases with age.

*Lenticels*.—Average number 51 in a 25.8 sq cm section. Average length 3.0 mm. Average width 1.7 mm. Color varies from 10YR 8/8 to 2.5Y 8/8.

*Color*.—New growth varies from 2.5GY 5/6 to 5GY 6/6. Old growth varies from 10YR 3/2 to 10YR 3/4, varies with age of growth.

Leaves:

*Size*.—Large. Average length 159.7 mm. Average width 45.4 mm.

*Form*.—Lanceolate.

*Apex*.—Acuminate.

*Base*.—Cuneate.

*Margin*.—Serrulate.

*Thickness*.—Medium.

*Surface texture*.—Upper surface relatively smooth, slight indentation over midrib and leaf veins. Lower surface relatively smooth, except for small ridges created by midrib and pinnate venation. Both upper and lower surfaces glabrous.

*Petiole*.—Average length 11.6 mm. Average width 1.8 mm. Longitudinally grooved. Surface glabrous. Color varies from 2.5GY 5/6 to 2.5GY 5/8.

*Glands*.—Type — reniform. Size — large. Average length 1.3 mm. Average width 1.2 mm. Average number 3, varies from 1 to 4. Located primarily on the base of leaf the blade and upper portion of the petiole. Color varies from 2.5GY 5/6 to 2.5GY 5/8.

*Stipules*.—Average number 2. Average length 11.7 mm. Edges — pectinate. Color varies from 2.5GY 5/8 to 5GY 5/6.

*Color*.—Upper surface varies from 5GY 3/6 to 5GY 3/4. Lower surface varies from 5GY 4/4 to 5GY 3/4. Midvein color varies from 2.5GY 7/6 to 2.5GY 6/6.

Flower Buds:

*Size*.—Large. Average length 20.8 mm. Average width 10.3 mm.

*Hardiness*.—Hardy with respect to California winters.

*Form*.—Conical, becoming elongated before opening.

*Pedicel*.—Average length 5.6 mm. Average width 1.2 mm. Color varies from 2.5GY 7/6 to 2.5GY 5/6.

*Color*.—Varies from 7.5RP 6/10 to 5RP 7/10.

Flowers:

*Blooming period*.—Date of First Bloom Feb. 27, 2012. Date of Petal Fall Mar. 9, 2012, varies slightly with climatic conditions.

*Size*.—Large, showy: Average height 24.9 mm. Average diameter 61.7 mm.

*Petals*.—Normally 5, alternately arranged to sepals. Form — orbicular, narrows at point of attachment. Petal apex — rounded. Petal base — acuminate. Size — large. Average length 29.6 mm. Average width 25.3 mm. Arrangement — free. Margin — sinuate. Color varies from 5RP 7/6 to 5RP 9/2, color fades with age of flower. Both upper and lower surfaces glabrous.

*Sepals*.—Normally 5, alternately arranged to petals. Size — large. Average length 8.0 mm. Average width 7.5 mm. Shape — ovate, apex rounded. Margin — entire. Surface — upper surface glabrous, lower surface pubescent. Color — upper surface varies from 5GY 5/6 to 7.5R 3/4. Lower surface varies from 5R 3/2 to 5R 2/4.

*Stamens*.—Average number per flower 42. Average filament length 18.8 mm. On average, the stamens are below the height of the petals. Filment color varies from N 9.5/(white) to 5RP 7/4. Anther color varies from 5Y 8/8 to 7.5R 4/8.

*Pollen*.—Self fertile. Color varies from 2.5Y 7/10 to 2.5Y 6/10.

*Pistil*.—Number — normally 1. Surface pubescent. Average length 21.3 mm. Position of stigma an average of 1.3 mm below anthers. Surface pubescent. Color varies from 10Y 8/6 to 10Y 7/6.

*Fragrance*.—Wanting.

*Color*.—Varies from 5RP 8/4 to 5RP 7/6.

*Number flowers per flower bud*.—Normally 1.

*Pedicel*.—Average length 6.0 mm. Average width 1.4 mm. Color varies from 2.5GY 6/6 to 5GY 5/6.

Fruit:

*Maturity when described*.—Firm ripe and ready for consumption.

*Date of first picking*.—Jun. 23, 2012.

*Date of last picking*.—Jul. 1, 2012, varies slightly with climatic conditions.

*Size*.—Large. Average diameter axially 71.5 mm. Average transversely in suture plane 82.5 mm. Average weight 275.5 grams, varies slightly with fertility of the soil, amount of thinning and climatic conditions.

*Form*.—Globose.

*Suture*.—Distinct, extends from base to apex.

*Ventral surface*.—Relatively smooth.

*Apex*.—Rounded to very slight tip.

*Base*.—Retuse.

*Stem cavity*.—Rounded to slightly elongated in suture plane. Average depth 11.9 mm. Average diameter 10.2 mm.

Stem:

*Size*.—Medium. Average length 11.8 mm. Average diameter 3.3 mm.

*Color*.—Varies from 2.5GY 6/6 to 2.5GY 8/8.

Flesh:

*Ripens*.—Relatively even, slightly earlier at the apex.

*Texture*.—Firm, meaty, crisp.

*Fibers*.—Few, small, tender.

*Firmness*.—Firm, comparable to other commercial varieties.

*Aroma*.—Slight.

*Amydgalin*.—Undetected.

*Eating quality*.—Very good.

*Flavor*.—Very good.

*Juice*.—Moderate amount, enhances flavor.

*Acidity*.—Not available.

*Brix*.—Average Brix 10.5°, varies slightly with amount of fruit per tree and climatic conditions.

*Color*.—Varies from 2.5Y 7/10 to 5Y 7/8.

*Pit cavity*.—Average length 42.0 mm. Average width 30.1 mm. Average depth 12.2 mm. Color varies from 5Y 8/12 to 5Y 7/10.

Skin:

*Thickness*.—Medium.

*Surface*.—Relatively smooth.

*Pubescence*.—Moderate amount, very short.

*Tendency to crack*.—None.

*Color*.—Ground color varies from 2.5Y 8/10 to 5Y 8/8. Overspread with 7.5R 3/8 to 7.5R 3/10.

*Tenacity*.—Tenacious to flesh.

*Astringency*.—Undetected.

Stone:

*Type*.—Clingstone, medium adherence to the stone.

*Size*.—Large. Average length 41.3 mm. Average width 29.6 mm. Average thickness 23.3 mm.

*Form*.—Ovoid.

*Base*.—Flat to slightly rounded.

*Apex*.—Pointed. Average length 3.3 mm.

*Surface*.—Pitted throughout, pits vary from round to elongated.

*Sides*.—Unequal, one side extending further from suture plane.

*Ridges*.—Small, narrow ridge extending from base toward apex.

*Tendency to split*.—None.

*Color*.—Varies from 10YR 6/6 to 10YR 6/8 when dry.

Kernel:

*Size*.—Large. Average length 21.3 mm. Average width 12.4 mm. Average depth 7.3 mm.

*Form*.—Ovoid.

*Viability*.—Viable, complete embryo development.

*Skin color*.—Varies from 5Y 8.5/6 to 5Y 8/8.

Use:

*Dessert*.—Market — local and long distance.

Keeping quality: Good, held firm in cold storage for 3 weeks at 38° to 42° F. without internal breakdown or appreciable loss of flavor.

Shipping quality: Good, showed minimal skin scarring or bruising of flesh during picking, packing and shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program. No atypical resistances/susceptibilities have been noted under normal cultural practices.

The present new variety of peach tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of peach tree, (*Prunus persica*) substantially as illustrated and described.

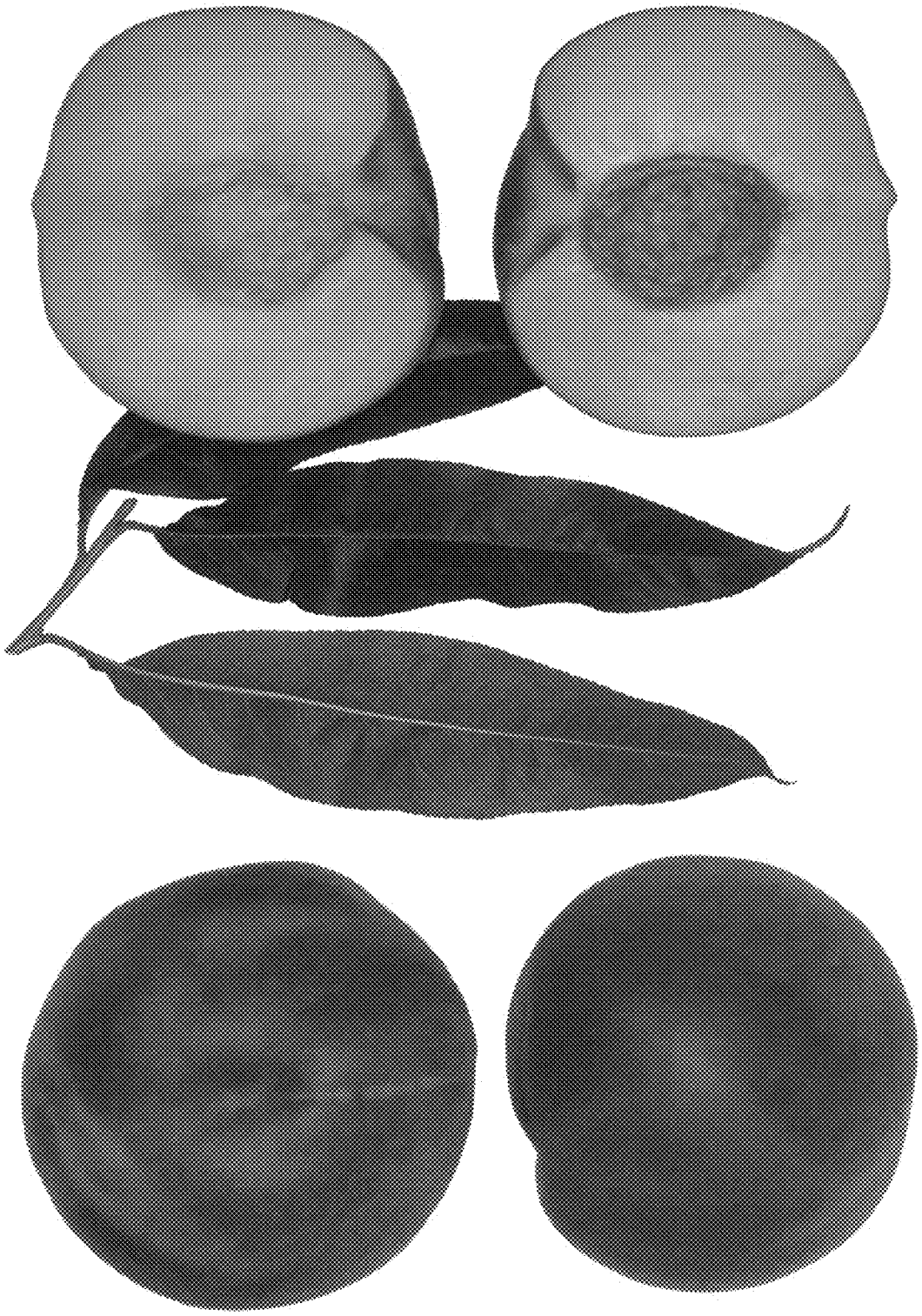

* * * * *